United States Patent
Moore et al.

(10) Patent No.: US 9,415,369 B2
(45) Date of Patent: *Aug. 16, 2016

(54) METHOD AND SYSTEM FOR THE ANALYSIS OF HIGH DENSITY CELLS SAMPLES

(71) Applicants: ACCUPATH DIAGNOSTIC LABORATORIES, INC., Irvine, CA (US); BIODOT, INC., Irvine, CA (US)

(72) Inventors: Mathew Moore, Irvine, CA (US); Miriam Reyes, Irvine, CA (US); David Baunoch, Irvine, CA (US); Thomas C. Tisone, Irvine, CA (US); Brendan O'Farrell, Irvine, CA (US)

(73) Assignees: Accupath Diagnostic Laboratories, Inc., Irvine, CA (US); BioDot, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/582,003

(22) Filed: Dec. 23, 2014

(65) Prior Publication Data

US 2015/0119283 A1    Apr. 30, 2015

Related U.S. Application Data

(63) Continuation of application No. 13/692,464, filed on Dec. 3, 2012, now Pat. No. 8,940,478, which is a continuation of application No. 12/833,879, filed on Jul. 9, 2010, now Pat. No. 8,323,882, which is a
(Continued)

(51) Int. Cl.
*G01N 33/569*    (2006.01)
*G01N 35/10*    (2006.01)
(Continued)

(52) U.S. Cl.
CPC ............ *B01J 19/0046* (2013.01); *C12Q 1/6841* (2013.01); *G01N 33/56966* (2013.01); *G01N 33/57415* (2013.01); *G01N 35/1016* (2013.01);
(Continued)

(58) Field of Classification Search
None
See application file for complete search history.

(56) References Cited

U.S. PATENT DOCUMENTS

| 4,575,490 A | 3/1986 | Ornstein et al. |
| 4,748,043 A | 5/1988 | Seaver et al. |

(Continued)

FOREIGN PATENT DOCUMENTS

| DE | 198 41 554 A1 | 3/2000 |
| DE | 199 05 490 A1 | 8/2000 |

(Continued)

OTHER PUBLICATIONS

Office action from European Patent Office in corresponding European Application No. 04 754 938.1, mailed Jun. 9, 2008, 5 pp.
(Continued)

*Primary Examiner* — Chris L Chin
(74) *Attorney, Agent, or Firm* — Knobbe, Martens, Olson & Bear LLP (57) ABSTRACT

Methods for forming cell arrays of multiple cell samples arranged substantially in a monolayer on a single substrate particularly suited for diagnostic analysis are disclosed. The cell arrays are formed with a high-speed dispensing apparatus capable of dispensing small volumes in precise, complex patterns. Also disclosed are substrates upon which cell arrays may be formed, and methods for conducting diagnostic analyses on the formed cell arrays.

18 Claims, 2 Drawing Sheets

Related U.S. Application Data continuation of application No. 10/866,513, filed on Jun. 10, 2004, now Pat. No. 7,754,439.

(60) Provisional application No. 60/477,807, filed on Jun. 12, 2003.

(51) Int. Cl.
  *B01J 19/00* (2006.01)
  *C12Q 1/68* (2006.01)
  *G01N 33/574* (2006.01)

(52) U.S. Cl.
  CPC . *B01J 2219/0061* (2013.01); *B01J 2219/00315* (2013.01); *B01J 2219/00378* (2013.01); *B01J 2219/00398* (2013.01); *B01J 2219/00527* (2013.01); *B01J 2219/00547* (2013.01); *B01J 2219/00576* (2013.01); *B01J 2219/00585* (2013.01); *B01J 2219/00596* (2013.01); *B01J 2219/00605* (2013.01); *B01J 2219/00612* (2013.01); *B01J 2219/00619* (2013.01); *B01J 2219/00637* (2013.01); *B01J 2219/00641* (2013.01); *B01J 2219/00659* (2013.01); *B01J 2219/00689* (2013.01); *B01J 2219/00691* (2013.01); *B01J 2219/00698* (2013.01); *B01J 2219/00743* (2013.01); *Y10S 436/809* (2013.01)

(56) References Cited

U.S. PATENT DOCUMENTS

| | | | |
|---|---|---|---|
| 5,008,185 | A | 4/1991 | Bacus |
| 5,041,266 | A | 8/1991 | Fox |
| 5,132,097 | A | 7/1992 | Van Deusen et al. |
| H1099 | H | 9/1992 | Sayler |
| 5,257,657 | A | 11/1993 | Gore |
| 5,445,934 | A | 8/1995 | Fodor et al. |
| 5,486,337 | A | 1/1996 | Ohkawa |
| 5,509,966 | A | 4/1996 | Sykes |
| 5,658,802 | A | 8/1997 | Hayes et al. |
| 5,707,588 | A | 1/1998 | Tsukishima |
| 5,741,554 | A | 4/1998 | Tisone |
| 5,743,960 | A | 4/1998 | Tisone |
| 5,744,305 | A | 4/1998 | Fodor et al. |
| 5,776,748 | A | 7/1998 | Singhvi et al. |
| 5,891,712 | A | 4/1999 | May |
| 5,981,733 | A | 11/1999 | Gamble et al. |
| 6,004,617 | A | 12/1999 | Schultz et al. |
| 6,063,339 | A | 5/2000 | Tisone et al. |
| 6,103,479 | A | 8/2000 | Taylor |
| 6,121,048 | A | 9/2000 | Zaffaroni et al. |
| 6,168,915 | B1 | 1/2001 | Scholl et al. |
| 6,215,894 | B1 | 4/2001 | Zeleny et al. |
| 6,220,075 | B1 | 4/2001 | Papen et al. |
| 6,232,066 | B1 | 5/2001 | Felder et al. |
| 6,287,850 | B1 | 9/2001 | Besemer et al. |
| 6,296,809 | B1 | 10/2001 | Richards et al. |
| 6,309,831 | B1 | 10/2001 | Goldberg et al. |
| 6,358,682 | B1 | 3/2002 | Jaffee et al. |
| 6,387,707 | B1 | 5/2002 | Seul et al. |
| 6,391,623 | B1 | 5/2002 | Besemer et al. |
| 6,416,952 | B1 | 7/2002 | Pirrung et al. |
| 6,521,187 | B1 | 2/2003 | Papen |
| 6,537,505 | B1 | 3/2003 | LaBudde et al. |
| 6,548,263 | B1 | 4/2003 | Kapur et al. |
| 6,576,295 | B2 | 6/2003 | Tisone |
| RE38,281 | E | 10/2003 | Tisone |
| 6,710,335 | B2 | 3/2004 | Ellson et al. |
| 6,713,021 | B1 | 3/2004 | Shvets et al. |
| 6,797,945 | B2 | 9/2004 | Berggren et al. |
| 6,838,051 | B2 | 1/2005 | Marquiss et al. |
| 6,881,579 | B2 | 4/2005 | Hilson et al. |
| 6,890,485 | B1 | 5/2005 | Stylli et al. |
| 6,916,620 | B2 | 7/2005 | Qiao et al. |
| 6,929,944 | B2 | 8/2005 | Matson |
| 6,995,024 | B2 | 2/2006 | Smith et al. |
| 7,141,368 | B2 | 11/2006 | Fisher et al. |
| 7,179,423 | B2 | 2/2007 | Bohm et al. |
| 7,199,809 | B1 | 4/2007 | Lacy et al. |
| 7,211,223 | B2 | 5/2007 | Fouillet et al. |
| 7,312,068 | B2 | 12/2007 | Pinkel et al. |
| 7,332,347 | B2 | 2/2008 | Li et al. |
| 7,442,499 | B2 | 10/2008 | Brown et al. |
| 7,754,439 | B2 | 7/2010 | Moore et al. |
| 8,323,882 | B2 * | 12/2012 | Moore ............... B01J 19/0046 435/4 |
| 8,940,478 | B2 * | 1/2015 | Moore ............... B01J 19/0046 435/287.2 |
| 2002/0064482 | A1 | 5/2002 | Tisone et al. |
| 2002/0092366 | A1 | 7/2002 | Brock et al. |
| 2002/0127565 | A1 | 9/2002 | Cunningham et al. |
| 2002/0151085 | A1 | 10/2002 | Zaffaroni et al. |
| 2002/0158027 | A1 | 10/2002 | Moon et al. |
| 2002/0159919 | A1 | 10/2002 | Churchill et al. |
| 2002/0168297 | A1 | 11/2002 | Shvets et al. |
| 2003/0143756 | A1 | 7/2003 | Fisher et al. |
| 2003/0148538 | A1 | 8/2003 | Ng |
| 2003/0175163 | A1 | 9/2003 | Shvets et al. |
| 2003/0228241 | A1 | 12/2003 | Legge |
| 2004/0009611 | A1 | 1/2004 | Williams et al. |
| 2004/0052955 | A1 | 3/2004 | Tisone |
| 2004/0072364 | A1 | 4/2004 | Tisone et al. |
| 2004/0091398 | A1 | 5/2004 | Gilbert et al. |
| 2004/0265185 | A1 | 12/2004 | Kitagawa |
| 2005/0003458 | A1 | 1/2005 | Moore et al. |
| 2005/0042767 | A1 | 2/2005 | Machida et al. |
| 2005/0232823 | A1 | 10/2005 | Brock et al. |
| 2006/0211132 | A1 | 9/2006 | Miledi et al. |
| 2006/0240400 | A1 | 10/2006 | Yamato et al. |
| 2006/0263264 | A1 | 11/2006 | Bohm et al. |
| 2007/0249060 | A1 | 10/2007 | Kirschner et al. |
| 2008/0226498 | A1 | 9/2008 | Stylli et al. |

FOREIGN PATENT DOCUMENTS

| | | |
|---|---|---|
| EP | 1 179 364 A2 | 2/2002 |
| EP | 1 179 368 A2 | 2/2002 |
| EP | 1 179 368 A3 | 10/2002 |
| EP | 1 179 364 A3 | 2/2003 |
| EP | 1 658 894 A1 | 5/2006 |
| WO | WO 99/34931 A1 | 7/1999 |
| WO | WO 03/072258 A1 | 9/2003 |

OTHER PUBLICATIONS

Office action from European Patent Office in corresponding European Application No. 04 754 938.1, mailed May 26, 2011, 4 pp.

Hansson, A. et al.;"Analysis of proliferation, apoptosis and keratin expression in cultured normal and immortalized human buccal keratinocytes"; Eur J Oral Sci; Feb. 2003; Abstract.

Wilson, W. Cris, Jr. et al; Cell and Organ Printing 1: Protein and Cell Printer: The Anatomical Record Part A 272A: 491-496 (2003).

\* cited by examiner

METHOD AND SYSTEM FOR THE ANALYSIS OF HIGH DENSITY CELLS SAMPLES

CROSS-REFERENCE TO RELATED APPLICATIONS

This application is a continuation of U.S. patent application Ser. No. 13/692,464, filed Dec. 3, 2012, which is a continuation of U.S. patent application Ser. No. 12/833,879, filed Jul. 9, 2010, now U.S. Pat. No. 8,323,882 B2, issued Dec. 4, 2012, which is a continuation of U.S. patent application Ser. No. 10/866,513, filed Jun. 10, 2004, now U.S. Pat. No. 7,754,439 B2, issued Jul. 13, 2010, which claims priority to U.S. Provisional Patent Application Ser. No. 60/477,807, filed Jun. 12, 2003, the teachings of each one of which are incorporated herein in their entirety.

BACKGROUND OF THE INVENTION

1. Field of the Invention

The present invention relates generally to a method for forming cell arrays on a substrate to facilitate high-throughput diagnostic analysis of a plurality of cell samples and, in particular, to cell arrays in which the discrete cell samples are arranged substantially in a monolayer with positive and negative controls, as well as test samples, arranged on the same substrate. More particularly, the present invention relates to cell arrays comprising multiple test and control samples arranged on a single substrate upon which immunohistochemistry, fluorescent in situ hybridization, and cytogenetic analyses may be conducted.

2. Description of the Related Art

Clinical analysis of cell samples obtained from patient specimens are routinely conducted by medical personnel and are useful tools for diagnosing and treating various diseases and medical conditions. Techniques for conducting clinical analyses have become increasing sophisticated as advances in medicine have led to methods of early detection and diagnosis of diseases and medical conditions. Such sophisticated techniques include, for example, immunohistochemistry (IHC) and fluorescent in situ hybridization (FISH), which can be useful for diagnosing diseases, such as cancer. Additionally, cytogenetic assays can be useful for diagnosing diseases and medical conditions associated with chromosomal aberrations, such as, for example, Down's syndrome.

As increasingly sophisticated techniques for detecting and diagnosing diseases and medical conditions have become routine, there is increased interest in simplified procedures for conducting these techniques that do not rely on the highly trained skills of medical personnel, thereby allowing the possibility of dramatically increasing the number of samples that can be analyzed at the same time. Traditionally, diagnostic assays such as IHC, FISH and cytogenetic assays are performed on a substrate, usually a glass microscope slide, containing one sample per slide. The single sample per slide may be either a patient sample or a control sample, which is analyzed in conjunction with the results of the patient sample to mitigate the risk of false positives. Typically, cell samples, whether they be control or patient samples, are applied to the microscope slide using a non-standardized drop method.

Unfortunately, the current state of the art methods for dispensing drops of cells onto microscope slides suffer from high variability due to the individual techniques employed by various operators. Typically, large drops in the range of 10-100 µL are dropped onto a slide and allowed to flow across the surface of the slide with the hope that a uniform distribution of the cells will result. In order to obtain optimum results, the environment in which the drops are applied to the slides must be carefully controlled with respect to temperature and humidity. However, these methods are considered more of an art than a science and frequently result in considerable overlap of cells and non-uniform dispersal of the cells across the surface of the substrate. Overlap and non-uniformity may lead to inefficient or insufficient interaction between a test reagent and a target, which may ultimately lead to poor detection and a misdiagnosis.

The diagnostic assays for use with the cell arrays contemplated herein typically involve the use of antibodies, enzymes, fluorophores, chromogens and other expensive reagents. Accordingly, it is advantageous to conduct the assay in as small a volume as possible to minimize costs. For example, a routine IHC assay requires a series of steps, including procuring cells from a biological sample, depositing the cells onto a substrate, and processing the cell sample so that it is ready to receive a test reagent or probe. The probe is generally incubated with the cell sample prior to removal of excess probe and addition of a detection reagent, such as an antibody, that recognizes the interaction between the probe and the protein of interest. Finally, an oil coating may be applied to the substrate to prevent evaporation and a cover slip added to the slide to facilitate image analysis, either through a microscope or an automated imaging system. A typical IHC assay conducted on a glass slide generally requires an area of about 25×50 mm, requires the use of between about 50-100 µL of reagent per assay, and requires multiple glass slides in order to process multiple samples.

The variability arising from the application of cell samples to the surface of the substrate may lead to increased variability in the results of the clinical assays and ultimately to inaccurate diagnoses. By contrast, a more ideal result is consistent application of cell samples (patient and control) to provide a uniform distribution of cells arranged substantially in a monolayer at a particular location on the substrate. An even more ideal result is the ability to miniaturize the process such that multiple samples can be included on the same substrate. In this way, for example, several patient samples can be subjected to the desired assay on the same slide as the control samples. An additional benefit of the miniaturization process is to decrease the quantity of sample and reagent needed to conduct the diagnostic assay, thereby decreasing the cost of the test while at the same time increasing the number of assays that can be performed with higher fidelity.

SUMMARY OF THE INVENTION

The cell arrays of the present invention overcome many of the drawbacks associated with current methods for conducting diagnostic assays. For example, the cell arrays formed according to the present invention may comprise as many as about 1000 discrete cell samples suitable for diagnostic analysis on a single substrate. Additionally, the cell arrays of the present invention are particularly suited for high-throughput diagnostic analyses, such as, for example, immunohistochemistry (IHC), fluorescent in situ hybridization (FISH), and cytogenetic analyses. Yet another advantage of the cell arrays of the present invention is the ability to conduct the desired diagnostic analysis on a single substrate that includes positive or negative control samples on the same substrate as the test samples.

In one innovative aspect, a cell array comprising a plurality of discrete cell samples on a single substrate may be formed by mixing a cell suspension in a source to obtain a substantially uniform distribution of the cells within the suspension; aspirating the cell suspension from the source; movably transporting the cell suspension relative to the substrate; metering a predetermined amount of the cell suspension using a positive displacement pump; and dispensing the metered amount of the cell suspension in the form of droplets onto the substrate so as to form a plurality of discrete cell samples in which each discrete cell sample is arranged substantially in a monolayer on the single substrate. In another embodiment, the method also includes the steps of treating the cell suspension to minimize cell clumping and lysis prior mixing the cell suspension. In certain embodiments, the steps of metering a predetermined amount of the cell suspension and dispensing the cell suspension may be repeated, while in other embodiments, the steps of transporting the cell suspension may be repeated along with the metering and dispensing steps. In yet other embodiments, the mixing, aspirating, transporting, metering, and dispensing steps may be repeated to form the cell array.

In additional embodiments, the method may further comprise the step of dispensing a predetermined amount of a cover fluid sufficient to substantially cover the plurality of discrete cell samples arranged on the single substrate. The cover fluid may be inert liquids, immiscible liquids, or mineral oil. In alternative embodiments, the cell array may comprise at least one test sample and at least one control sample. In certain embodiments, the substrate upon which the cell array is formed may be a glass slide, a nitrocellulose membrane, a plastic membrane, a nylon membrane, or a nylon membrane on a continuous roll. In certain embodiments, the method may comprise the step of coating a surface of the substrate with a surface modifier prior to dispensing the cell suspension onto the substrate. The surface modifier may be poly-L-lysine, amines, streptavidin, epoxy, metal film, or dielectric materials. In additional embodiments, the substrate may be a glass slide comprising a barcode region, a control region, and a test region, in which the barcode region may have at least a slide tracking barcode or a dispense and lock barcode.

In another embodiment, the method may comprise the step of coating a surface of the glass slide with a hydrophobic layer in the control region and the test region prior to conducting the dispensing step. The hydrophobic region may be configured with a plurality of openings passing substantially through the hydrophobic layer to the surface of the glass slide. In yet another embodiment, the predetermined amount of the cell suspension is dispensed in a volume between about 1 nL to about 500 nL having a density of between about 200 to about 400 cells per 100 nL with each dispensed discrete cell sample occupying a location on the substrate having a diameter of about 1 mm or less.

The present invention also contemplates a method for conducting a diagnostic analysis on a cell array. In one embodiment, the method may comprise the steps of forming the cell array comprising a plurality of discrete cell samples on a single substrate; contacting the cell array with at least one test reagent sufficient to detect the presence of a predetermined analyte; allowing a reaction to occur between the test reagent and the predetermined analyte; and detecting the reaction between the test reagent and the predetermined analyte, such that the reaction between the test reagent and the predetermined analyte is sufficient to provide a diagnosis. According to this embodiment, the method for forming the cell array may comprise the steps of mixing a cell suspension in a source; aspirating the cell suspension from the source; movably transporting the cell suspension relative to the substrate; metering a predetermined amount of the cell suspension using a positive displacement pump; and dispensing the metered amount of the cell suspension in the form of droplets onto the substrate so as to form a plurality of discrete cell samples, such that each discrete cell sample is arranged substantially in a monolayer on the substrate. In another embodiment, the method also includes the steps of treating the cell suspension to minimize cell clumping and lysis prior mixing the cell suspension. In certain embodiments, the steps of metering a predetermined amount of the cell suspension and dispensing the cell suspension may be repeated, while in other embodiments, the steps of transporting the cell suspension may be repeated along with the metering and dispensing steps. In yet other embodiments, the mixing, aspirating, transporting, metering, and dispensing steps may be repeated to form the cell array. In certain embodiments, the step of allowing the reaction to occur between the test reagent and predetermined analyte may comprise heating at least one discrete cell sample on the substrate.

In additional embodiments, the method for conducting a diagnostic analysis may further comprise the step of dispensing a predetermined amount of a cover fluid sufficient to substantially cover the plurality of discrete cell samples arranged on the single substrate. The cover fluid may be inert liquids, immiscible liquids, or mineral oil. In alternative embodiments, the cell array may comprise at least one test sample and at least one control sample. In certain embodiments, the substrate upon which the cell array is formed may be a glass slide, a nitrocellulose membrane, a plastic membrane, a nylon membrane, or a nylon membrane on a continuous roll. In certain embodiments, the method may comprise the step of coating a surface of the substrate with a surface modifier prior to dispensing the cell suspension onto the substrate. The surface modifier may be poly-L-lysine, amines, streptavidin, epoxy, metal film, or dielectric materials. In additional embodiments, the substrate may be a glass slide comprising a barcode region, a control region, and a test region, in which the barcode region may have at least a slide tracking barcode or a dispense and lock barcode. In one embodiment, the diagnostic analysis is fluorescent in situ hybridization and the test reagent is a nucleic acid probe; in another embodiment, the diagnostic assay is an immunohistochemistry assay and the test reagent is an antibody probe; in yet another embodiment, the diagnostic assay is a cytogenetic assay and the test reagent is a chromosome stain.

In other embodiments, a cell array upon which a diagnostic assay may be conducted in accordance with the present invention may comprise a plurality of discrete cell samples on a single substrate, with the cells of each discrete cell sample arranged substantially in a monolayer on the substrate. In another embodiment, the single substrate may also comprise a barcode region, a test region, and a control region. The barcode region may comprise at least one of a slide tracking barcode, and a dispense and lock barcode. In yet another embodiment, a reaction between a test reagent and a predetermined analyte within the plurality of discrete cell samples of the control region may generate a pattern detectable by an imaging system such that the pattern is sufficient to uniquely identify the substrate upon which the cell array is formed. In one embodiment, the control region of the cell array may comprise between about 1 to about 1000 discrete cell samples.

In certain embodiments, the plurality of discrete cell samples may comprise at least one test sample and at least one control sample on the single substrate. In yet another embodiment, the diagnostic assay may be immunohistochemistry, fluorescent in situ hybridization, or cytogenetic analysis. In still another embodiment, each discrete cell sample of the cell array may have a diameter of less than about 1 mm and may be formed from a dispensed droplet having a volume of between about 50 to about 200 nL. In yet another embodiment, the substrate may comprise a glass slide, a nitrocellulose membrane, a plastic membrane, a nylon membrane, or a nylon membrane on a continuous roll. In some embodiments, the cell array may be covered with a cover fluid. The cover fluid may be inert liquids, immiscible liquids, or mineral oil.

In another embodiment, the substrate upon which the cell array is formed is a glass slide having a surface that may comprise a hydrophobic layer configured with a plurality of openings for accepting the discrete cell samples in the test region and control region, in which the plurality of openings passing substantially through the hydrophobic layer to a surface of the glass slide. In yet another embodiment, the hydrophobic layer on the glass slide has about 105 openings for accepting the discrete cell samples in the sample region and control region in which each opening is capable of accepting a volume of between about 1 nL to about 500 nL, and each opening has a diameter of about 1 mm or less.

In another innovative aspect, a substrate of the present invention upon which a cell array may be formed may comprise a barcode region, a control region, and a test region, in which the cell array may comprise a plurality of discrete cell samples arranged substantially in a monolayer, and the barcode region may comprise at least one of a slide tracking barcode, and a dispense and lock barcode. In one embodiment, the density of the discrete cell samples on the substrate is between about 50 to about 105 discrete cell samples per substrate and each discrete cell sample occupies a location on the substrate having a diameter of about 1 mm or less. In another embodiment, the discrete cell samples are formed from a droplet of a cell suspension having a volume of between about 50 to about 200 nL. In still another embodiment, the substrate may be a glass slide, a nitrocellulose membrane, a plastic membrane, a nylon membrane, or a nylon membrane on a continuous roll. In yet another embodiment, the substrate is a glass slide having a surface that is coated with a hydrophobic layer in the control region and the test region, and the hydrophobic layer is configured with a plurality of openings passing substantially through the hydrophobic layer to the surface of the glass slide, with each opening capable of accepting the discrete cell samples arranged substantially in a monolayer. In still another embodiment, the hydrophobic layer has a density of about 1500 openings, each opening is about 1 mm or less in diameter and is capable of accepting a volume of between about 50 to about 200 nL. In certain embodiments, the substrate is coated with a surface modifier that may comprise poly-L-lysine, amines, streptavidin, epoxy, metal film, or dielectric materials. In another embodiment, the substrate is adapted to provide heating to at least one discrete cell sample.

In still another innovative aspect of the invention, the present invention provides for a method for forming a cell array under a cover fluid, in which the cell array may comprise a plurality of discrete cell samples on a single substrate. The method may comprise covering the substrate with a cover fluid so that a surface of the cover fluid is exposed; mixing a cell suspension within a source; aspirating the cell suspension from the source; movably transporting the cell suspension relative to the substrate; metering a predetermined amount of the cell suspension using a positive displacement pump; and dispensing the metered amount of the cell suspension in the form of droplets from a non-contact dispenser at a controlled velocity onto the surface of the cover fluid so that the droplets penetrate the surface of the cover fluid and form a plurality of discrete cell samples, in which each discrete cell sample is arranged substantially in a monolayer on the substrate. In one embodiment, the method may additionally comprise aspirating at least one test reagent from a source; and dispensing the test reagent onto a plurality of the discrete cell samples of the cell array. In another embodiment, the method may also include detecting a reaction between the test reagent and a predetermined analyte within the discrete cell samples of the cell array. In certain embodiments, the method may comprise the step of treating the cell suspension to minimize clumping and lysis prior to conducting the mixing step.

Finally, in still another aspect of the invention, the present invention provides for a method for forming a cell array for cytogenetic analysis comprising a plurality of cells arranged substantially in monolayer on a single substrate. The method may comprise the steps of mixing a cell suspension in a source to obtain a substantially uniform distribution of the cells within the source; aspirating the cell suspension from the source; movably transporting the cell suspension relative to the substrate; metering a predetermined amount of the cell suspension using a positive displacement pump; and dispensing the metered amount of the cell suspension in the form of droplets onto the substrate so as to form a plurality of discrete cell samples, with each discrete cell sample being arranged substantially in a monolayer on the substrate, and the distance between the discrete cell samples minimized such that the perimeter of each discrete cell sample is contiguous with the perimeter of an adjoining discrete cell sample. In one embodiment, the method may also comprise the step of treating the cell suspension to minimize cell clumping and lysis prior to conducting the mixing step. In another embodiment, the method may comprise the step of repeating at least step the dispensing step to form the cell array. In yet another embodiment, the method may comprise the step of repeating at least the transporting, metering, and dispensing steps to from the cell array. In yet another embodiment, the method may comprise the step of repeating the mixing, aspirating, transporting, metering and dispensing steps to from the cell array.

Those of skill in the art will appreciate that the invention described herein may be embodied or carried out in a manner that achieves or optimizes one advantage or group of advantages taught herein without necessarily achieving other advantages as may be taught or suggested herein. All of these embodiments are intended to be within the scope of the invention disclosed herein. These and other embodiments of the present invention will become readily apparent to those skilled in the art from the following detailed description of the preferred embodiments having reference to the attached figures, the invention not to be limited to any particular preferred embodiment disclosed.

DETAILED DESCRIPTION OF THE PREFERRED EMBODIMENTS

System Overview

A dispensing apparatus of the present invention is particularly well suited for forming cell arrays having a plurality of cell samples arranged substantially in a monolayer on a single substrate. Cells arranged substantially in a monolayer are cells that are relatively uniformly dispersed with sufficiently low minimal overlap on the surface of the substrate such that an imaging system can accurately and rapidly inspect the three-dimensional morphology of individual cells and detect signal resulting from the interaction of a test reagent and a predetermined analyte or target within the cells. The dispensing apparatus is also well suited for dispensing test reagents onto the plurality of cell samples after formation of the cell array. Typically, patient or test samples, as well as positive and negative control samples, comprise the cell array formed on the single substrate.

Figure 1:
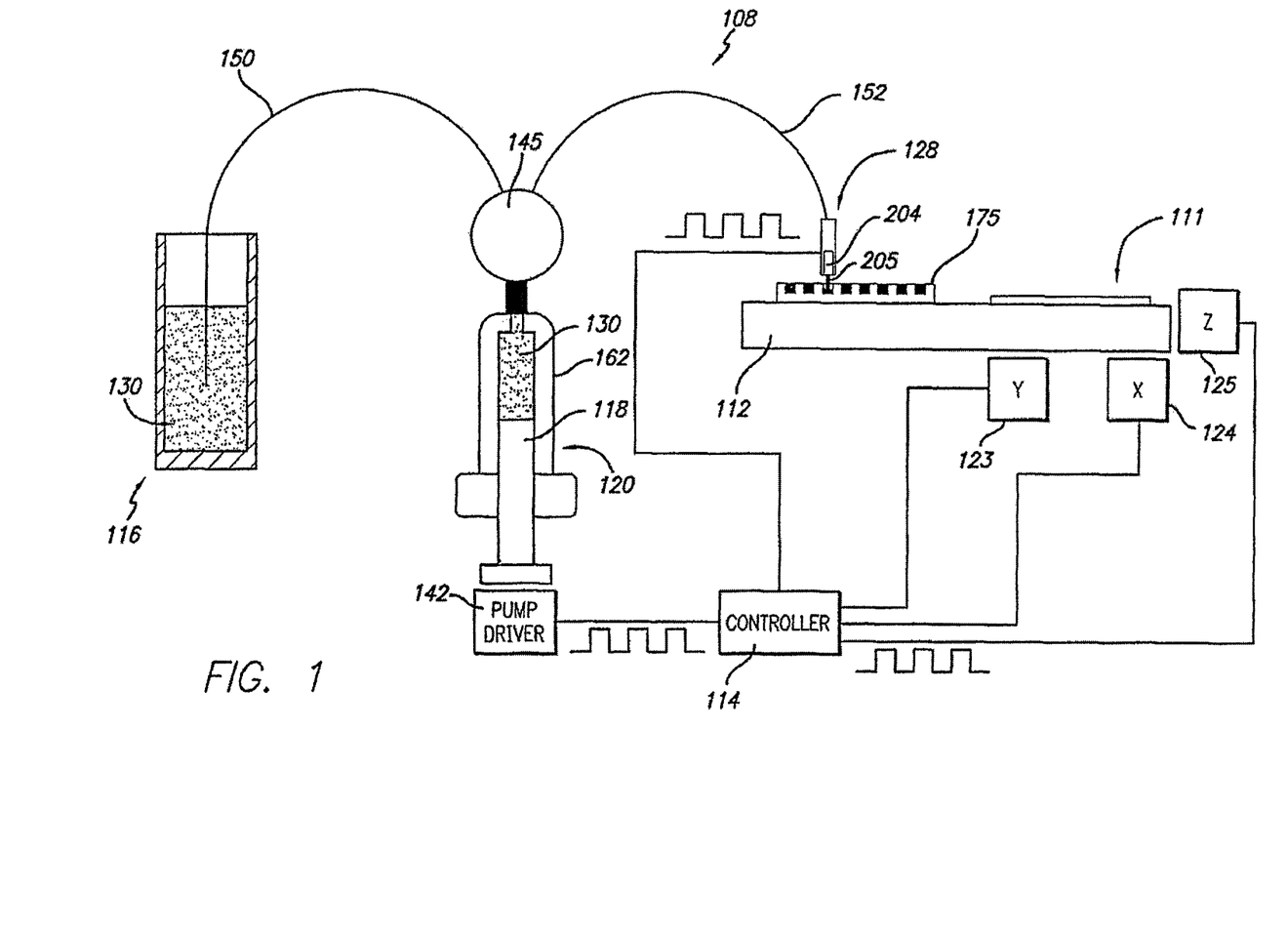
FIG. 1. is a schematic generalization of a dispensing apparatus having features and advantages in accordance with the present invention.

As shown in FIG. 1, the dispensing apparatus 108 generally comprises a dispensing head or dispenser 128 having a valve or other dispensing means 204 operated by an actuator, such as, for example, a solenoid that dispenses drops onto a substrate 111 in a non-contact manner. The dispenser 128 is hydraulically coupled or in fluid communication with a positive displacement pump 120 for metering precise quantities of fluid or liquid 130 to or towards the dispenser 128. The dispensing head 128 is mounted on or in association with an X-Y-Z platform 112. The term "X-Y-Z platform" as used herein refers to a platform that is capable of moving in the X, Y, and/or Z directions in any combination. The X-Y-Z platform 112 may include one or more position stepper motors 123, 124, 125 or the like, which are operable to move either the dispensing head 128 and/or the X-Y-Z platform 112 relative to one another in the X, X-Y, or X-Y-Z directions. It bears noting also that while this description may refer only to a single dispensing head 128, it is contemplated that multiple dispensing heads in linear (1.times.N) or two-dimensional arrays (M.times.N) can also be used with equal or improved efficacy. Such multiple dispensing heads may be operated in parallel, i.e., for multi-gang operation, or in another coordinated fashion, as desired.

One or more substrates 111 may be mounted on the X-Y-Z platform 112 to receive reagent dispensed from the dispenser 128. Additionally, a source reservoir 175 may be mounted on the X-Y-Z platform 112 from which reagents may be aspirated by the dispenser 128 and dispensed onto the substrate 111. It should be understood that while a single source reservoir 175 and a single substrate 111 are depicted in FIG. 1, multiple sources and multiple substrates may be mounted or arranged on the X-Y-Z platform 112 as desired. Frequently, the source reservoir 175 will be a microplate but may be any suitable reservoir that temporarily stores reagents to be dispensed onto the substrate 111 by the dispenser 128. Similarly, it should be understood that the term "reagent" as used herein refers to cell suspensions or test reagents that will be dispensed by the dispenser 128 onto the substrate 111.

The substrate 111 may comprise any suitable surface upon which a cell array may be formed and a diagnostic assay may be conducted. Exemplary substrates include, but are not limited to, nylon membranes, plastic membranes, nitrocellulose membranes, and glass slides. In certain embodiments, the substrate 111 may comprise a membrane, such as nylon, that is fed from a continuous roll.

The positive displacement pump 120 preferably comprises a syringe pump, although other direct current fluid sources may be used. The syringe pump 120 is hydraulically coupled to or in fluid communication with a fluid reservoir 116 through a first supply line 150 and a switching valve 145. The syringe pump 120 draws fluid 130 from the fluid reservoir 116 and provides it to or toward the dispensing head 128 through a second supply line 152 also in communication with switching valve 145.

The syringe pump 120 has a movable piston 118 within a syringe barrel 162. The syringe pump 120 is operated by a syringe pump driver 142 comprising, for example, a stepper motor and an associated lead screw, for extending and retracting the piston 118 within the syringe barrel 162. Those skilled in the art will readily appreciate that when the piston 118 is retracted, fluid 130 is drawn from the reservoir 116 through the switching valve 145 into the syringe pump 120. When the piston is again extended, fluid 130 is forced to flow from the syringe barrel 162 into the dispensing head 128 via the second supply tube 152, whereupon it is ejected by the dispensing head 128 onto the substrate 111 in the form of droplets.

In one embodiment, the fluid 130 comprises the reagent that is dispensed onto the substrate 111. Thus, the reservoir 116, pump barrel 162, dispenser 128 and supply lines 150 and 152 are filled with the fluid 130 to be dispensed. This arrangement is particularly advantageous when large quantities of the same reagent are to be dispensed onto the substrate 111. For example, it may be desirable to manufacture large number of substrates each having an identical pattern of positive and negative controls arranged thereon for use by a reference laboratory, which may later add patient or test samples and conduct diagnostic analyses.

In another embodiment, the fluid 130 comprises a backing reagent, such as distilled water, and the dispensing apparatus 108 operates in an aspirate/dispense mode. In this embodiment, the dispenser 128 is used to aspirate a predetermined amount of reagent from the source reservoir 175, movably transport the reagent relative to the substrate 111, meter the predetermined amount of the reagent, and dispense the aspirated reagent onto or into the substrate 111. Reagent is aspirated by retracting or decrementing the pump piston 118 with the switching valve 145 open to create a reduced pressure or partial vacuum along supply line 152 to draw reagent from the source reservoir 175 into the dispenser 128 via a suitable tip 205 or nozzle thereon. In certain embodiments, this same process can be repeated on a smaller scale to mix reagent, particularly cells that may have settled out of solution so as to provide a relatively homogenous cell suspension which then may be aspirated and subsequently dispensed onto the substrate 111. As will be appreciated, it may be necessary to repeat some or all of the steps in order to form the desired cell array and/or dispense the desired test reagents necessary for the diagnostic analysis onto the cell array after it is formed.

A controller 114 oversees operation of the syringe pump 120, X-Y-Z platform 112, and the dispensing head 128. Specifically, the controller 114 coordinates and controls the motion of each of the stepper motors 123, 124, 125 and the syringe pump driver 142, as well as the opening and closing of the dispensing valve 204 to precisely meter and dispense an amount of reagent at one or more predetermined location(s) on the substrate 111. As necessary, the controller 114 also controls and coordinates mixing and aspiration of reagent from the source reservoir 175. A software program is interfaced with the controller 114 to guide mixing, dispensing, and aspirating for different modes of operation and different applications. As is discussed more fully below, a user-defined text file is preferably generated, for example, from a spreadsheet of values or a template, with lists of numbers of user-defined dispense volumes for one or more reagents and corresponding coordinates of the mixing, aspirating, and dispensing operation. The controller 114 uses this text file data in cooperation with the software program to precisely control and coordinate the operation of the dispensing apparatus 108.

The dispensing apparatus 108 may operate in "step and repeat" mode or, alternatively, "on-the-fly," that is without stopping the motion of the X-Y-Z platform 112. To accommodate this on-the-fly dispensing without sacrificing accuracy, precision or repeatability, the controller 114 calculates a phase adjustment for each dispense cycle. The phase adjustment is such as to advance or retard the timing of the valve 204 opening and closing so that the dispensed droplet of reagent lands at the desired location on the substrate 111 (or at a desired offset location), taking into account its anticipated trajectory.

Those skilled in the art will appreciate that the magnitude of the necessary or desired phase adjustment will depend, among other things, on a number of system input and output parameters and behavioral characteristics, including the desired drop offset (if any), the vertical distance between the dispensing head nozzle 205 and the surface of the substrate 111, the velocity and/or acceleration of the dispensing head 128 and/or the substrate 111 relative to one another, the velocity of the dispensed droplets, ambient temperature and humidity, and other controlled and/or uncontrolled factors. While certain of these parameters or characteristics can be isolated and studied such that their impact on the necessary phase adjustment is fairly predictable, other parameters or characteristics can neither be isolated nor predicted. Precise phase adjustments can be determined experimentally for a given production set up either before or during production such that a high degree of accuracy, precision, and repeatability is attained during long production runs.

One of the advantages of forming a cell array using the dispensing apparatus 108 described herein is a cell array in which each discrete cell sample is assigned its own address on the substrate 111. Once the array is contacted with the desired test reagents, an imaging system can be implemented to precisely, accurately, and rapidly move about the substrate 111 to detect a reaction between the test reagent(s) contacted with the cell array and a predetermined analyte(s) or target(s) within the cells of the array. The imaging system used to analyze the cell arrays of the present invention may be a microscope or an automated machine capable of detecting a reaction between the test reagent and the predetermined analyte. Such a reaction may include the emission of fluorescence, light, radioactivity, or the like.

As will be appreciated by one of skill in the art, if the cell array is to be used for diagnoses based on fluorescent in situ hybridization assay, the predetermined analyte or target within the cell samples may be a particular gene that can be detected with a commercially available nucleic acid probe. Similarly, if the cell array is to be used for diagnoses based on an immunohistochemistry assay, the predetermined analyte or target within the cell samples may be a particular protein that can be detected with a commercially available antibody. The antibody may be primarily labeled or capable of being detected with a subsequent reagent. Additionally, if the cell array is to be used for diagnosis based on a cytogenetic assay, the predetermined analyte is a chromosome that can be stained with a commercially available chromosome staining reagent. One of ordinary skill in the art will appreciate that the present invention is not limited to particular diagnostic assays that can be performed on a cell array, nor is the present invention intended to be limited to any particular predetermined analyte, whether commercially available or otherwise. Indeed, the cell arrays formed according to the methods described herein are amenable to any type of diagnostic assay that benefits from discrete cell samples arranged substantially in a monolayer on a single substrate.

Dispensing Devices

The present invention incorporates the use of methods and devices for non-contact dispensing drops of reagent onto a substrate 111 to form a cell array upon which diagnostic assays, such as, for example, immunohistochemistry (IHC), fluorescent in situ hybridization (FISH), and cytogenetic analyses can be performed. The methods and devices used to dispense the cell suspension and any subsequent test reagents in a non-contact fashion onto the substrate are not critical to present invention, and one of skill in the art will appreciate that many methods and devices may be used to generate such cell arrays and dispense such test reagents. Accordingly, the present invention is not intended to be limited to a particular method or device for generating cell arrays or conducting diagnostic assays on a substrate; however, particularly preferred are the methods and devices developed by Biodot, Inc. (Irvine, Calif.).

As shown in FIG. 1, the dispensing apparatus 108 may be implemented using any one of a number of commercially available reagent dispensers, piezoelectric dispensers, solenoid valve dispensers, and the like, although a solenoid valve dispenser is preferred for general applications. While the selection of the dispenser head 128 is not critical to practicing the present invention, it has been found that a solenoid actuated valve dispenser provides good results when used in accordance with the teachings herein. Those of skill in the art will appreciate that other types of dispensers and valve actuation devices exist and may be used efficaciously. Examples of dispensers that may be used in the present invention include, for example, air brush dispensers, piezoelectric dispensers, fluid impulse dispensers, heat actuated dispensers, and the like.

A positive displacement pump 120 provided in series with the dispenser 128 allows metering of a predetermined amount of the dispensed reagent (which may be measured by quantity or flow rate) to be controlled independently of the particular flow characteristics of the liquid being dispensed and/or the operating parameters of the particular dispenser 128. For example, the size of the droplets formed by the dispenser 128, and hence the number of cells dispensed onto the substrate 111, can be adjusted by changing the operating frequency (for a solenoid valve or piezoelectric dispenser) or by adjusting the air pressure or exit orifice size (for an airbrush dispenser) without affecting the flow rate of the reagent. Moreover, the reagent flow rate can be controlled independent of the system operating parameters otherwise required to achieve stable dispensing operations. The amount of reagent dispensed, in terms of quantity or flow rate, is controlled independently by the positive displacement pump 120. As used herein, the term "reagent" can mean either a cell suspension or a test reagent to be dispensed onto the cell array that is formed.

Still referring to FIG. 1, the pump 120 is preferably a high-resolution, positive displacement syringe pump 120 hydraulically coupled to the dispenser 128. Alternatively, the pump 120 may be any one of several varieties of commercially available pumping devices for metering precise quantities of liquid. A syringe-type pump 120, as shown for example in FIG. 1, is preferred because of its convenience and commercial availability. A wide variety of other direct current fluid source means may be used, however, to achieve the benefits and advantages as disclosed herein. These may include, without limitation, rotary pumps, peristaltic pumps, squash-plate pumps, and the like, or an electronically regulated fluid current source.

Several suitable syringe pumps are commercially available. For example, the Biodot CV1000 Syringe Pump Dispenser, available from Biodot, Inc. (Irvine, Calif.) incorporates an electronically controlled stepper motor for providing precision liquid handling using a variety of syringe sizes. The CV1000 is powered by a single 24 DC volt power supply and it controlled via an industry-standard RS232 or RS485 bus interface. The syringe pump 120 may have anywhere from 3,000-24,000 steps, although higher resolution pumps having 48,000-768,000 steps may be used with the present invention. Higher resolution pumps, such as, for example, piezoelectric pumps may also be used to provide even finer resolutions, if desired. Multiple syringe pumps may be employed in parallel, for example, to deliver varying concentrations of reagents and/or other liquids to the dispenser or to alternate dispensing operations between two or more reagents as may be desired when conducting the diagnostic assays contemplated by the present invention.

The reagent reservoir 116 may be any one of a number of suitable receptacles capable of allowing a liquid reagent to be siphoned into the pump 120. The reservoir 116 may be pressurized, as desired, but is preferably vented to the atmosphere. The particular size and shape of the reservoir 116 is relatively unimportant. Cell suspensions to be dispensed onto or into the substrate 111 may be placed in a microplate or similar source 175 prior to being dispensed through the dispenser 128 onto or into the substrate 111 to form the cell array.

Controller

In one preferred embodiment of the present invention, the dispensing apparatus 108 uses a controller 114 which generally comprises a host CPU or computer that interfaces with some form of data memory. In particular, the controller may be divided into five basic subsystems: host CPU, coordinate control circuitry, memory and logic circuitry, syringe stop count circuitry, and valve firing circuitry. Those of skill in the art will appreciate that each subsystem works in cooperation with the other subsystems to simultaneously control and coordinate the stepper motors 123, 124, 125, the syringe pump motor 142, and the valve dispenser 128 to precisely mix, aspirate, transport, meter, and dispense an amount of reagent at one or more predetermined locations on or in the substrate 111. The controller 114 may also coordinate and control wash/purge operations and refilling the dispensing apparatus with fluid from the fluid reservoir 116, as needed or desired.

In another preferred embodiment, more fully disclosed in co-pending U.S. patent application Ser. No. 09/945,388, filed Aug. 30, 2001, published under Publication No. US 2002/0159919 on Oct. 31, 2002 and entitled METHOD AND APPARATUS FOR HIGH-SPEED MICROFLUIDIC DISPENSING USING TEXT FILE CONTROL, incorporated herein by reference, the dispensing apparatus 108 is equipped with a controller 114 that interfaces with a computer software program to guide dispensing and/or aspirating for different modes of operation of the system and different applications. Preferably, a user-defined text file is generated, for example, from a spreadsheet of values or template, with lists of number of user-defined dispense volumes of one or more reagents and corresponding coordinates of the dispense and/or aspirate operation. The controller 114 uses this text file data in cooperation with the software program to precisely control and coordinate the operation of the dispensing apparatus 108.

One advantage of using text file control in conjunction with the aspirate/dispense apparatus and operations of the embodiments described herein is that complex patterns of dispense location and droplet volume can be easily achieved through, for example, a spreadsheet template. This is particularly useful for "combinatorial" dispensing applications in which "n" number of test reagents are combined in different ratios and applied to the discrete cell samples of the cell array. For example, the user may desire to dispense two or more test reagents to a particular set of discrete cell samples comprising the cell array. The user may custom-design the combinatorial experiment using the text file and/or spreadsheet format and then easily download the experiment to the software which will be executed by the controller 114. In situations where "combinatorial" dispensing is desired, more than one dispenser, a manifold system, or a combination thereof may be utilized to facilitate process efficiency. Configurations employing multiple dispensers may be operated in parallel or in synchronous coordination.

Operation

Conceptually, the substrate 111 upon which the cell array is to be formed and upon which the diagnostic assays are to be performed is divided into rows (X-axis) and columns (Y-axis) having a predetermined resolution in terms of a number of addressable target locations per linear distance "d." Thus, a linear distance d equal to one inch (2.54 cm) of substrate 111 traveling along one axis may, for example, contain 100-500 or more individually addressable target locations. Each target location would correspond to a number of X-axis stepper motor 123 increments and a number of Y-axis stepper motor 124 increments relative to a predetermined "zero" position.

Because each target location has a unique address, the controller 114 is able to precisely select particular target location(s) in which to dispense predetermined amounts or droplets of a cell suspension or test reagent(s). In one embodiment, a preferred pattern of dispensing motion in relation to the substrate 111 advantageously decreases the time to complete a particular dispensing operation. Upon executing a first linear pass along a first row, the dispensing head 128 reverses direction and executes a second pass along an adjacent second row. Such bi-directional dispensing advantageously decreases the time required to complete a dispensing operation in comparison to a unidirectional dispensing operation. It is also envisioned that for non-sequential or intermittent dispensing the controller 114 would speed operation by dispatching the dispensing head 128 directly to or adjacent the next desired target location without necessarily completing each successive pass or each intervening row.

The coordinates of the target locations can be used by the imaging system which can be rapidly deployed to a particular X-Y location on the substrate 111 and detect the reaction, if any, between the test reagent(s) and the predetermined analyte(s) for each cell within the discrete cell samples forming the cell array. It will be appreciated that the imaging system may also scan for the presence of a reaction at multiple Z positions within a given cell. Arranging the cells substantially in a monolayer facilitates not only access of the test reagent(s) to each cell, but also detection of any reactions by the imaging system.

As is described more fully in U.S. Pat. No. 6,576,295, the entirety of which is hereby incorporated by reference, the dispensing apparatus 108 may operate to dispense relatively large quantities of the same reagent in a continuous dispensing mode, in which the syringe pump 120 is set to a prescribed flow rate to deliver a predetermined metered amount of reagent expressed as volume-per-unit time. For example, the flow rate could be programmed to deliver 1 μL per second. The syringe pump 120 will then pump reagent to the solenoid valve 204 at the predetermined rate. By opening and closing the valve 204 during this flow, droplets will be formed according to the open time and operating frequency of the valve 204. Thus, in continuous dispensing mode, the dispensing apparatus 108 is not only capable of delivering precise metered flow rates of reagent, but the delivery can be accomplished with independent control of X-Y-Z platform 112 speed, reagent concentration per unit length and droplet size. The continuous dispensing mode may be particularly useful to form a large number of substrates each having identical patterns of positive and negative controls, to which patient or test samples may be added at a later time. This mode of dispensing is also referred to as "on-the-fly" dispensing.

The dispensing apparatus 108 may also operate in dot dispensing mode, in which individual droplets may be dispensed at pre-programmed locations. This can be accomplished by synchronizing the solenoid valve 204 and the syringe pump 120 with the X-Y-Z platform 112. The syringe pump 120 is incremented to generate a hydraulic pressure wave. The solenoid valve 204 is coordinated to open and close at predetermined times relative to the pump 120 increment. The valve 204 may initially be opened either before or after the pump 120 is incremented. While the valve 204 is open the pressure wave pushes a volume of fluid down the nozzle 205 forming a droplet at the exit orifice at the time of peak pressure amplitude. The droplet will have a size determined by the incremental volume provided by the syringe pump 120. Such a drop will be dispensed onto the substrate 111 without the need for the nozzle 205 to contact the substrate 111. This mode of dispensing is sometimes referred to as "step and repeat" mode.

In still another embodiment, the dispensing apparatus 108 operates in aspirate and dispense mode. In this mode, precise quantities of fluid, cell suspension, or test reagent are aspirated, i.e., "sucked," from a source 175, such as, for example, a microplate. Particularly when the dispensing apparatus 108 is dispensing cells to the substrate 111, the aspirate and dispense mode may mix the cell suspension to form a substantially homogeneous suspension within the source reservoir 175 prior to aspiration from the source reservoir 175 onto the substrate 111. The dispenser 128 may be a simple nozzle or needle or, more preferably, it may be a solenoid valve dispenser 204. The syringe pump 120 and dispenser 128 are preferably synchronized or coordinated with the X-Y-Z movable platform 112. The same dispenser 128 can further be used to aspirate one or more test reagents at precisely the same locations as the cell suspensions. A wash cycle can be implemented into the process to clean the dispenser 128 to minimize the possibility of contamination.

Generally, the syringe pump 120 is filled with a wash fluid, such as distilled water. The tip 205 of the dispenser 128 is placed into the cell suspension source reservoir 175 and the syringe pump 120 is decremented to draw a precise, metered amount of the cell suspension into the tip 205 of the dispenser 128. It is generally desirable only to aspirate a small volume of cell suspension into the tip 205 of the solenoid valve dispenser 128 so that the cell suspension does not pass into the valve 204. The syringe pump 120 is then incremented to dispense a precise amount of the cell suspension at a predetermined location on the substrate 111. The remaining cell suspension can be dispensed to the next predetermined location or dispensed into a waste receptacle along with a predetermined quantity of the wash. This ensures that the cell suspension sample does not get diluted with the wash fluid and the cell suspension is flushed out after each aspirate and dispense mode. It may be necessary to repeat some or all of the mixing, aspirating, transporting, metering, and dispensing steps in order to achieve a cell array having the desired dimensions. After the cell array is formed in this manner, the dispenser 128 is able to mix, aspirate, and dispense one or more test reagents to the plurality of discrete cell samples comprising the cell array as needed or desired following substantially the same process.

In another preferred embodiment, more fully described in U.S. Patent Application No. 60/359,471, filed Feb. 22, 2002 published under International Publication No. WO 03/072258 on Sep. 4, 2003, the entirety of which is hereby incorporated by reference, droplets of the cell suspension used to form the cell array and/or droplets of the test reagents used to conduct the diagnostic assays may be dispensed below the surface of a cover fluid using the non-contact dispensing devices described herein. A substrate having a cover fluid minimizes evaporation of valuable test reagents used in the diagnostic assay. Dispensing reagents through a cover fluid also has the advantage, in the case of miscible reagents, of providing mixing action of the test reagent and the target as a result of the velocity of the drop as it passes through the cover fluid.

Platform

The X-Y-Z platform 112 may include one or more position stepper motors 123, 124, 125 or the like, which are operable to move either the dispenser 128 and/or the X-Y-Z platform 112 relative to one another in the X, X-Y, and/or X-Y-Z directions. The controller 114 is adapted to receive data representative of a desired dispensing pattern and to provide first, second, and third signals for causing relative motion between the substrate 111 and the dispenser 128 while simultaneously causing the dispenser 128 to dispense the droplets (containing cell suspension or test reagent) at one or more desired locations on the substrate 111 to form the desired patterns.

Additionally, one or more robot arms may be used, according to need or desire, to provide controlled relative motion between the dispenser 128 and the substrate 111 and/or other components of the dispensing apparatus 108. Moreover, in some embodiments, the platform 112 is adapted to provide heating to predetermined locations on the substrate 111 so as to facilitate diagnostic assays that may require a source of heat, for example, PCR, in order to function efficaciously. Heat may also be used to increase the hybridization kinetics, for example, in a FISH assay. Methods and devices for providing a heat source to a predetermined location on a platform are well known in the art (e.g., heated pins, thin film heaters and the like) and can be incorporated into the dispensing apparatus 108 described herein with relative ease.

The dispensing apparatus 108 system is not limited to a single dispenser 128. In some embodiments, it is contemplated that multiple dispensers in linear (1.times.N) or two-dimensional (M×N) arrays are used. Such multiple dispensers may be provided and operated either in parallel or in another coordinated fashion, as desired. It is to be understood that any discussion herein with specific reference to a single dispenser embodiment is substantially equally applicable, with possible modifications apparent to those of skill in the art, to embodiments having multiple dispensers each connected to respective pump devices or a single pump device.

In still another embodiment, multiple substrates may be arranged on the X-Y-Z platform 112 to allow multiple cell arrays to be generated simultaneously. In such an embodiment, multiple dispensers can be independently moved or operated together in the form of a dispense head comprising multiple dispense channels separated from one another by predetermined distances. Additionally, the dispensers can be individually operated (serially or sequentially) or substantially simultaneously, for example, in parallel, or in any combination as needed. A main controller, possibly in conjunction with sub-controllers, is used to control and coordinate actuations of the pump device and relative movement between the target substrate and dispense channels. Certain embodiments of a multi-channel aspirate-dispense system comprising a manifold of multiple dispense channels are more fully described in co-pending U.S. patent application Ser. No. 09/372,719, filed Aug. 11, 1999, entitled MULTI-CHANNEL DISPENSING SYSTEM, the entirety of which is hereby incorporated by reference.

In yet another embodiment, one or more pressure sensors are provided in conjunction with the aspirate-dispense device 108 to monitor the system pressure and provide diagnostic information about various fluid and flow parameters within the hydraulic system. The one or more pressure sensors are placed between the syringe pump(s) 120 and the dispenser(s) 128, such as, for example, on the supply line 150, 152. Alternatively, or in addition, the pressure sensor(s) can be situated at the dispenser(s) 128, such as, for example, on the valve portion(s) 204.

Cell Arrays

Cell arrays generated using the dispensing apparatus 108 described herein may be formed with droplet volumes as small as about 1 nL, 5 nL, 10, nL, 25 nL, or 50 nL. Typically, droplet volumes may range from about 1 nL to about 500 nL, although preferred droplet volumes range from about 100 nL to about 500 nL; more preferred droplet volumes range from between about 100 nL to about 250 nL. This small droplet volume allows multiple discrete cell samples to be applied to a single substrate 111, such as a microscope slide, so that between about 1-5, 5-10, 10-100, 500-1000 or more, discrete samples, including a combination of patient and control samples, may be formed on the single substrate 111. The small sample volume also significantly reduces the amount of test reagent that is necessary for the diagnostic assay, thereby further decreasing the overall cost of conducting the diagnostic assay while at the same time increasing the fidelity of the results of the diagnostic assay because the patient and control samples can be processed under identical conditions. The test reagent(s) used with the present invention may be dispensed in the same droplet volumes previously described for cell sample droplet volumes.

The typical velocity at which a droplet is dispensed from the dispenser may range from about 1 m/s to about 4 m/s, which is sufficient to dispense the reagent (either cell suspension or test reagent) without causing any splashing. Additionally, this range of velocities may be sufficient to cause mixing in those embodiments in which a test reagent is dispensed through a cover fluid at a particular location on the substrate. Other velocities may be used according to need or desire.

It is frequently desirable to treat the cell suspension to minimize clumping and/or lysis of the cells prior to dispensing the cells onto the substrate 111. One method to minimize clumping and/or lysis of the cell suspension is to replace the media of the cell suspension with a solvent, such as, for example, ethanol, methanol, propanol, acetic acid or any combination thereof. Replacing the media of the cell suspension with alcohol or the like also facilitates uniform distribution of the dispensed cells onto the substrate, thereby aiding in formation of a substantial monolayer on the substrate 111. Typically, replacing the cell media involves serial passages of the cells through solutions having increasing concentrations of alcohol until the desired concentration of cells and alcohol is reached. Any solvent may be used provided that it does not disturb the integrity of the cells or interfere with the ability of the test reagent(s) to interact with the predetermined analyte(s). Alcohol is preferred because it helps to minimize cell overlap and evaporates quickly. Typically, cells are passed through increasing concentrations of alcohol ranging from about 35% to about 65%, although alcohol concentrations outside this range may be used as needed or desired.

Typically, cell suspensions to be arranged in an array comprising a plurality of discrete cell samples on a single substrate 111 are transferred from a source 175, such as, for example, one or more microplates. In order to re-suspend cells that may have settled prior to dispensing onto the substrate 111, the cell suspension may be mixed to form a substantially homogenous population of cells within the source 175. Typically, mixing is accomplished by placing the dispenser tip 205 into the source 175 and conducting several small aspirate/dispense cycles within the source 175.

Depending on the density of the cells within the suspension, it may be desirable to dilute the cells prior to dispensing onto the substrate. It is preferable to dispense the cells so that the distance between adjacent cells in each discrete sample is between about 50 to about 100 microns. It is also preferable to dispense between about 200 to about 1000 cells per discrete sample to provide statistically relevant analysis. Typically a 100 nL drop of cells spaced about 100 microns apart will dry in an area having a diameter of about 1 mm. Accordingly, it is preferable to achieve a cell suspension density of between about 200 to about 1000 cells per 100 nL. Drop volumes can be adjusted as necessary to provide a sufficient monolayer distribution of cells on the substrate.

Generally, between about 200 to about 400 cells will provide a statistically significant sample population from which an accurate diagnosis may be made based on the result of the diagnostic assay. The sample population may be configured as described above, i.e., a discrete cell sample comprising between about 200 to about 400 cells in a single spot on the substrate. Alternatively, the sample population may be configured as a plurality of discrete cell samples, each sample comprising a smaller number of cells, which, when analyzed together comprise a statistically significant population. For example, one discrete cell sample comprising 200 cells from patient A would be equivalent to 10 discrete cell samples each comprising 20 cells from patient A. Any number of permutations and combinations can be configured to provide an overall population of cells, which, when analyzed, provides a statistically significant sample population from which an accurate diagnosis may be made. In situations in which it is desirable to reduce the number of cells per discrete cell sample, the volume of the droplet containing the cells may be similarly reduced.

A typical cell array formed on a single substrate as described herein will have at least one test sample and at least one control sample. However, as many as about 1000 test samples and about 100 control samples may comprise the cell array. A cell array comprising between about 10 to about 100 test samples and between about 2 to about 20 control samples is preferred. Other configurations having between about 1-5, 5-10, 10-20, 20-50, 50-75, 75-100, 100-200, 200-500 or more test samples with between about 1-5, 5-10, 10-20, 20-50, 50-75, 75-100, 100-200, 200-500 or more control samples may be used. Any combination of test samples and control samples may be formed, limited only by the physical dimensions of the substrate, the volume of the droplets to be dispensed onto the substrate and the desired distance between each discrete cell sample.

A typical cell array formed on a single substrate as described herein may be probed with at least one test reagent or a multiple of test reagents at each discrete cell sample. One of skill in the art will appreciate that any number of test reagent(s) can be used per each discrete cell sample, as needed or desired, up to the ability of the imaging system to detect the reaction between the test reagent(s) and the predetermined analyte of the cells. Typically, test reagent(s) are dispensed in drops with volumes ranging from about 1 nL to about 1 µL, although volumes between about 50 nL to about 500 nL and between about 100 nL to about 250 nL are preferred.

Typical cytogenetic analyses are conducted on a plurality of cells taken from the same source, i.e., the same patient or cell line. In addition to the methods described herein, a cell array suitable for cytogenetic analysis may be formed as a plurality of discrete samples in which the distance between the discrete cell samples is minimized such that the outer perimeter of each discrete cell sample is contiguous with the perimeter of an adjoining discrete cell sample. For example, a cell suspension droplet volume of about 50 nL with a distance between discrete cell samples of about 500 microns will result in a cell array in which the outer perimeter of each discrete cell sample being contiguous with the perimeter of adjoining discrete cell samples. Similarly, it is possible to achieve the same configuration by increasing the cell suspension drop volume and the spacing between the discrete cell samples, e.g., providing a cell suspension drop volume of about 400 nL and a distance of between about 1000-1200 microns between discrete cell samples. This configuration, in which the outer perimeter of each discrete cell sample is contiguous with the perimeter of an adjoining discrete cell sample, results in a cell array arranged substantially in a monolayer that covers a substantial portion of the substrate 111. One benefit to forming the cell array using the methods described herein is that the high-speed, precision dispensing apparatus facilitates accurate placement of the cells on the substrate and concomitant arrangement of the cells substantially in a monolayer. A control region may not be needed on the substrate when a cell array is intended to be used for cytogenetic analyses.

Substrate

The cell arrays of the present invention may be formed on a variety of substrates 111. A preferred substrate is a glass microscope slide, but other substrates, such as, for example nitrocellulose membranes, nylon membranes, and plastic membranes may be used with similarly efficacious results. In some embodiments, the substrate, generally a nylon membrane, may be continuously fed from a roll. In some embodiments, the surface of the substrate may be coated with a surface modifier that facilitates the arrangement of the cells substantially in a monolayer. Suitable surface modifiers include, but are not limited to, poly-L-lysine, amines, streptavidin, epoxy, thin metal films, dielectric materials, and the like.

Figure 2:
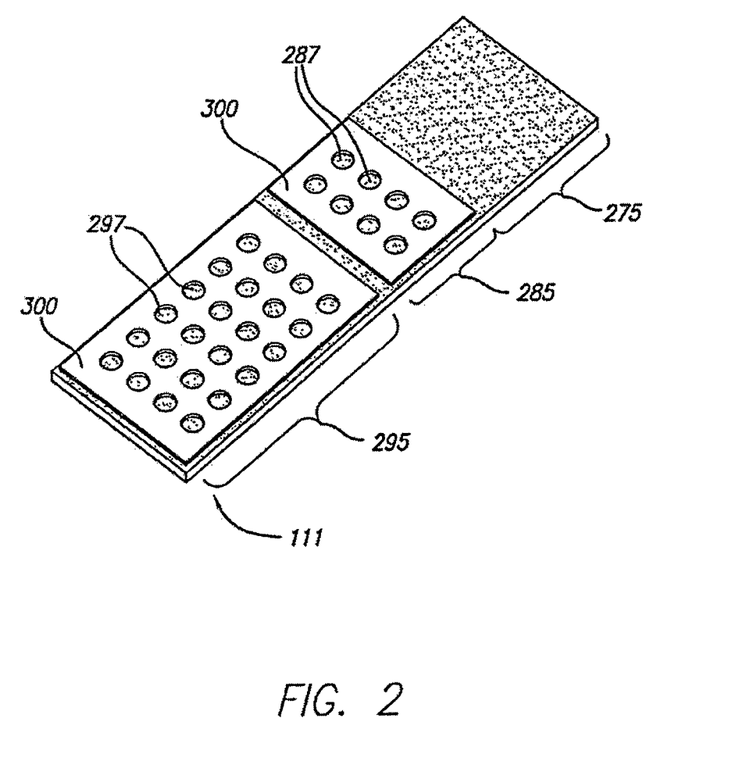
FIG. 2. is a schematic illustrating a cell array comprising a plurality of discrete cell samples on a single substrate having features and advantages in accordance with the present invention.

In one embodiment, as shown in FIG. 2, the substrate 111 comprises three separate regions, a barcode region 275, a control region 285, and a test region 295. The barcode region 275 is designed to accommodate a barcode that uniquely identifies each particular substrate 111. In addition, the barcode region 275 can accommodate a "dispense and lock" barcode, which serves as a security feature to ensure that the particular substrate 111 will work only in conjunction with the dispensing apparatus 108 described herein. Alternatively, or in addition, the barcode region may accommodate a slide tracking barcode that serves to identify the particular slide. Barcodes may be imprinted or otherwise arranged on the barcode region of the substrate according to methods known in the art.

The control region 285 on the substrate 111 may contain either or both positive and negative cell samples in any combination. The discrete cell samples 287 in the control region 285 are arranged substantially in a monolayer, that is, relatively uniformly dispersed with sufficiently minimal overlap such that an imaging system can accurately and rapidly inspect the three dimensional morphology of the cells and detect signal resulting from the interaction of a test reagent and a predetermined analyte or target within the cell. Arranging the positive and negative control samples on the same substrate 111 as the test or patient samples increases the overall fidelity of the diagnostic assays performed on the resulting cell array because the test samples 297 are processed in the same fashion and on the same substrate 111 as the control samples 287. The control region 285 can be configured to host as few as one control sample 287 (which may be either a positive or negative control) or in excess of 1000 control samples 287 as needed or desired. In some embodiments, it may be desirable to form a control region having between about 1-5, 5-10, 10-20, 20-50, 50-75, 75-100, 100-200, 200-500 or more discrete control samples, which may be any combination of positive and negative controls. Preferably, however, the control region 285 hosts between about 2 to about 20 discrete cell samples 287, which may be any combination of positive and negative controls, as needed or desired. The discrete cell samples 287 may, in some embodiments, be used as a source of data from which a standard curve may be generated for use with the diagnostic assay provided that the emissions resulting from the interaction between the test reagent and the predetermined analyte are capable of quantitation.

The test region 295 on the substrate 111 can host patient or test samples 297. As in the control region 285, the discrete cell samples 297 in the test region 295 are arranged substantially in a monolayer. One of ordinary skill in the art will appreciate that the discrete cells 297 comprising the test region 295 (and/or the control region 285) may be all the same, i.e., multiple samples obtained from the same patient sample (or cell line), in which case the cell array can be used to determine the presence or absence of a variety of predetermined analytes or targets. Alternatively, the discrete samples 297 comprising the test region 295 may be from a plurality of patient samples (or cell lines) which can then be contacted with the same or different test reagents in order to process a multitude of patient samples simultaneously. As is apparent to one of ordinary skill in the art, numerous combinations of patient samples (or cell lines) may be used in conjunction with any numerous combinations of test reagents.

In another embodiment, which is illustrated in FIG. 2, the control region 285 and the test region 295 of the substrate 111 may be covered with a hydrophobic layer 300. The hydrophobic layer 300 serves to contain each particular discrete cell sample 287, 297 in a predetermined location on the substrate 111. The hydrophobic layer 300 has a plurality of openings that pass substantially through the hydrophobic layer 300 to the surface of the substrate 111. The surface modifiers described above may also be used in conjunction with the hydrophobic layer. Typically, the diameter of the opening ranges from about 250 microns to about 4000 microns. An opening of about 250 microns can accommodate a volume of up to about 5 nL, while an opening of about 4000 microns can accommodate a volume of up to about 3 µL. The diameter of the opening, and the volumes actually dispensed into each opening is largely a manner of preference. Similarly, the number of openings is largely a matter of preference, and almost any configuration is possible, including, for example, 5, 10, 15, 25, 50, 100, 105, 200, 250, 500 or more openings. For some applications, it may be preferable to configure the substrate with a number of openings that is some multiple of 96, which is common number of wells in a microtiter plate. Process by which a hydrophobic layer may be applied to the surface of the substrates are well known in the art.

In yet another embodiment, the discrete cell samples 287 of the control region 285 are probed with a combination of test reagents capable of reacting with a predetermined analyte within the cells comprising the array. The interaction between the test reagent and the predetermined analyte typically results in a signal, i.e., fluorescence, which can be detected by an imaging system. The detectable signal may result in a unique pattern referred to as a "biological barcode" which uniquely identifies a particular substrate 111. The biological barcode serves as an additional security feature because, in contrast to a traditional barcode imprinted on the substrate 111, the biological barcode is a measure of the integrity of the conditions under which the substrate 111 has been stored. That is, because the biological barcode is comprised of a plurality of control cells that have been probed with a plurality of test reagents identical to the test reagents in the test region 295 of the substrate 111, events that would destroy the integrity of the test region 295 will also likely destroy the integrity of the biological barcode.

The biological barcode may be formed, for example, by dispensing 10 discrete cell samples 287 in the control region 285 and probing each sample 287 with a combination of three positive test reagents resulting in $1.\times.10.\sup.4$ different combinations (i.e., each discrete sample can have one of four conditions: unprobed, probed with 1 test reagent, probed with 2 test reagents, and probed with 3 test reagents.) The combinations of test reagents dispensed can be randomized. As will be appreciated, increasing either the number of test reagents and/or the number of discrete cell samples 287 exponentially increases the number of possible combinations, which may be selected according to need or desire.

Example 1

Cell Array Formation

In order to conduct clinical diagnostic tests on several patient samples simultaneously, it is often desirable to map (replicate or transform) one or more microplate arrays into a high density cell array of discrete cell samples arranged substantially in a monolayer on a single substrate. The substrate containing the cell array can then be subjected to any number of clinical diagnostic tests that rely on detection of a reaction between a test reagent and a predetermined analyte within the cells of the array, particularly diagnostic assays that benefit from an even and uniform distribution of cells.

In one example, samples from three cell lines, CaSki, HeLa, and T24, were formed in a cell array arranged substantially in a monolayer on a single substrate. The cell array was formed with 4 discrete cell samples from each of the 3 cells lines, i.e., the cell array contained 12 discrete cell samples. Prior to forming the cell array, the cell lines had an initial concentration of 0.5 cells/nL. The number of cells dispensed to each discrete cell sample was expected to range from between about 50 to about 400 cells dispensed in drop volumes ranging between about 10 and 80 nL.

The cell samples were treated to prevent clumping and lysing prior to formation of the cell array. Specifically, the cell samples were centrifuged and resuspended in a 50% methanol solution to a total volume of 150 µL. The cells were allowed to equilibrate in the 50% methanol solution for about 20 minutes before dilution in absolute methanol to a final volume of 450 µL, resulting a final concentration of between about 40-50 cells per 10 nL.

A text file was written instructing the dispensing apparatus to aspirate from a source reservoir, meter, and dispense successively 10, 20, 40, and 80 nL droplets of cells onto 50 glass slides. Prior to aspiration, each of the cell suspensions was mixed. The backing solution in the fluid reservoir was ethanol, and methanol was used as the washing solution.

The 4×3 cell array was formed on each of two sets of 50 glass slides. The center-to-center distance between successive droplets of the same reagent was 5 mm, and the center-to-center distance between droplets of different reagents (with the same volume) was 10 mm. The resulting cell arrays were visually inspected. Each of the 12 discrete cell samples was arranged substantially in a monolayer on the glass slides.

In another example, it is possible to map four 96 well plates having 9 mm center-to-center well spacings into a 384 dot array on a single substrate having center-to-center spacings in the range of about 1500 microns and a spot volume of between about 1000 to about 1200 microns. One way to generate such a cell array is to successively operate one dispensing head at a time of an 8-head dispenser with 9 mm center-to-center head spacing using a synchronous line dispense mode with a large spacing between drops. A typical substrate upon which a cell array is formed is a standard 25×75 mm glass microscope slide. One can array 50 glass slides on an X-Y platform and operate each of 8 dispense heads in succession to produce droplets with a spacing in the range of 1.5 mm on each slide at the same position. The other 7 dispense heads can be operated in linear succession with small offsets to produce an array of 8 droplets on the glass slide with a small separation of between about 100-1000 microns between droplets. Note that this operation can be done using one dispense head at a time, or more preferably, using all 8 dispense heads in rapid succession with small time delays to provide the desired linear spacing. By repeating this function for all four microplates and using suitable offsets, one can map four microplates into a single 384 array on each glass slide. In this case, the map would be a miniaturized replica of each 96 well plate arranged in a 4×4 array.

The dispenser can also be programmed to transform one or more microplate arrays into a new or different high or low density array. For example, a series of two dimensional arrays may be transformed into rows or columns or a larger high-density array, or arrays may be transposed or inverted. Other modes and variations for the use and operation of the invention will be apparent to those of skill in the art.

Example 2

Dispensing Through a Cover Fluid

Some embodiments described herein relate generally to dispensing droplets and in particular to methods for mixing, aspirating, transporting, metering and dispensing droplets of cell suspension or test reagent below the surface of a cover fluid using without contacting the dispenser with the surface of the cover fluid in order to for a cell assay or to conduct a diagnostic assay. Advantageously, evaporation of valuable test regents and cell samples is substantially prevented or reduced by using a cover fluid. Another advantage, in the case of miscible reagents, is that the droplet velocities provide good mixing. Yet another advantage is that, in the non-contact dispensing scheme, the nozzle or tip is not immersed in the cover fluid, thereby facilitating cleaning.

Mineral oil may be used as a cover fluid over the cell array. Mineral oil is frequently used as an evaporation barrier. Typically, the cell array is formed on the substrate, and mineral oil is dispensed to cover the discrete cell samples. Thus, in one embodiment, the test reagents are dispensed through the mineral oil. One of skill in the art will appreciate that drops of reagents can be dispensed through a cover fluid provided that the density of the drops is higher than the density of the cover fluid. For example, 100 nL drops of test reagent(s) can be dispensed through a mineral oil cover layer onto the discrete cell samples of the array. In some embodiments, it is possible to selectively heat the discrete cell samples after the test reagent(s) have been dispensed through the mineral oil, thereby increasing the kinetics of the interaction between the test reagent and the predetermined analyte, which may increase the speed with which the diagnostic assay can be performed.

Example 3

Florescent In Situ Hybridization Analysis

In another embodiment of the invention, cell arrays are formed by replicating one or more microplate arrays onto or into a high density array on a substrate, such as, for example, a glass slide. A cell suspension containing cytogenetic preparations of 104 different cell cultures was placed into a 384 well plate. The density of the cell suspension was approximately $1 \times 10^8$ cells/mL. Approximately 500-1000 cells were mixed, aspirated, transported, metered, and dispensed through the dispensing apparatus onto the glass slide. The apparatus dispensed a drop volume of 100 nL. The cells comprising the array formed according to the methods described herein were counted and confirmed to be arranged substantially in monolayer on the substrate.

Additionally, cell arrays formed according to the methods described herein were subjected to FISH analysis using several commercially available DNA probes, including CEP3, CEP7, CEP17, 9p21, X and Y (Vysis, Inc., Downers Grove, Ill.). The CEP probes recognize chromosome-specific DNA sequences from highly repeated human satellite DNA, identification of cells in interphase and metaphase. All probes were used according to the manufacturer's instructions (Vysis, Inc., Downers Grove, Ill.). The slides were analyzed using the HYBrite Hybridization System according to the manufacturer's instructions (Vysis, Inc., Downers Grove, Ill.).

The cell array formed was highly amenable to FISH analysis. The results were comparable or superior to standard hybridization and analysis techniques. Analysis of the X and Y chromosomes showed 100% concordance with expected results, and fewer than 1% contamination of the Y chromosome was observed in any single preparation containing XX cells. Individual subcellular features remained distinct, even after the FISH assay, and the cells of the array remained adherent to the surface of the glass slide throughout the FISH procedure.

Example 4

Immunohistochemistry Analysis

The dispensing apparatus described herein was used to dispense a single row cell array in methanol onto a glass slide which was further subjected to immunohistochemistry (IHC) analysis according to techniques well known to those of skill in the art. Specifically, 500-1000 cells from each of four cells lines that are typically used by reference laboratories to diagnose breast cancer were dispensed in a single row array about 15 mm from the end of the glass slide. The following cell lines were used: MCF7, which is positive for estrogen receptor; T47D, which is positive for progesterone receptor; BT474, which overexpresses Her2; and K562, which is a negative control.

After the cell array was formed, the glass slide was dehydrated and fixed for 1 hour in a formalin solution. Following the fixation, the cell array was embedded in paraffin by dipping the end of the slide comprising the cell array into histology-grade paraffin wax for 2 minutes. Excess wax was removed from the surface of the glass slide with a scalpel. The cell array on the glass slide was de-paraffinized and subjected to standard antigen retrieval techniques before being loaded onto a BenchMark®Instrument (Ventana Medical Systems, Inc., Tucson, Ariz.) for automated IHC analysis. The results are summarized in the following table.

|       | Estrogen Receptor Expression | Progesterone Receptor Expression | Her2 Expression |
|-------|------------------------------|----------------------------------|-----------------|
| MCF7  | high                         | moderate                         | 0+              |
| T47D  | low                          | high                             | 1+              |
| BT474 | low                          | low                              | 3+              |
| K562  | none                         | none/low                         | 0+              |

The results are consistent with published data, indicating that cell arrays formed according to the methods of the present invention are suitable for use in IHC.

Example 5

Cytogenetic Analysis

A cell array for a cytogenetic analyses was prepared on a 2 mm.sup.2 area on a glass slide. A plurality of cells from the same source were mixed, aspirated, transported, metered, and dispensed in a drop volume of 400 nL. The distance between each spot was minimized to about 0.5 mm. There was observable overlap of the dispensed droplets, which could have been minimized by either increasing the distance between the drops or decreasing the drop volume. The resulting array comprised a population of cells arranged substantially in a monolayer and evenly dispersed across the glass slide. After the cell array was generated, the slide was subjected to cytogenetic banding techniques well known to those of skill in the art.

The results indicated that the cell array produced using the dispensing apparatus described herein yielded an array with more consistent density than was obtained using traditional techniques. A licensed technologist evaluated the morphology of the metaphase cells contained in the array and compared them to cells produced by traditional techniques; the technologist confirmed that the cell array generated according to the methods and system described herein was suitable for cytogenetic analysis.

While the present invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described.

What is claimed is:

1. A method for forming a cell array comprising a plurality of discrete cell samples on a single substrate, the method comprising the steps of:
   (a) mixing a cell suspension in a source to obtain a substantially uniform distribution of cells within the cell suspension;
   (b) aspirating the cell suspension from the source;
   (c) movably transporting the cell suspension relative to the substrate; and
   (d) dispensing a predetermined amount of the cell suspension in the form of droplets onto the substrate so as to form a plurality of discrete cell samples, each discrete cell sample arranged substantially in a monolayer on the single substrate.

2. The method of claim 1 further comprising the step of treating the cell suspension to minimize cell clumping and lysis prior to conducting step (a).

3. The method of claim 1 further comprising the step of repeating at least step (d) to form the cell array.

4. The method of claim 1 further comprising the step of dispensing a predetermined amount of cover fluid sufficient to substantially cover the plurality of discrete cell samples arranged on the single substrate, wherein the cover fluid is selected from the group consisting of inert liquids, immiscible liquids, and mineral oil.

5. The method of claim 1, wherein the cell array that is formed comprises at least one test sample and at least one control sample on the single substrate.

6. The method of claim 1, wherein the substrate is selected from the group consisting of a glass slide, a nitrocellulose membrane, a plastic membrane, a nylon membrane, and a nylon membrane on a continuous roll.

7. The method of claim 6 further comprising the step of coating a surface of the substrate with a surface modifier prior to conducting step (d), wherein the surface modifier is selected from the group consisting of poly-L-lysine, amines, streptavidin, epoxy, metal film, and dielectric materials.

8. The method of claim 1, wherein the substrate is a glass slide comprising a barcode region, a control region, and a test region, wherein the barcode region comprises at least one of a slide tracking barcode, and a dispense and lock barcode.

9. The method of claim 8 further including the step of coating a surface of the glass slide with a hydrophobic layer in the control region and the test region prior to conducting step (d), wherein the hydrophobic layer is configured with a plurality of openings passing substantially through the hydrophobic layer to the surface of the glass slide.

10. The method of claim 1, wherein the predetermined amount of the cell suspension is dispensed in a volume between about 1 nL to about 500 nL having a density of between about 200 to about 400 cells per 100 nl and wherein each dispensed discrete cell sample occupies a location on the substrate having a diameter of about 1 mm or less.

11. A method for conducting a diagnostic analysis on a cell array comprising the steps of:
   (a) forming the cell array comprising a plurality of discrete cell samples on a single substrate, the method for forming the cell array comprising the steps of:
      (i) mixing a cell suspension in a source;
      (ii) aspirating the cell suspension from the source;
      (iii) movably transporting the cell suspension relative to the substrate; and
      (iv) dispensing a predetermined amount of the cell suspension in the form of droplets onto the substrate so as to form a plurality of discrete cell samples, each discrete cell sample arranged substantially in a monolayer on the substrate;
   (b) contacting the cell array with at least one test reagent sufficient to detect the presence of a predetermined analyte;
   (c) allowing a reaction to occur between the test reagent and the predetermined analyte; and
   (d) detecting the reaction between the test reagent and the predetermined analyte, wherein the reaction between the test reagent and the predetermined analyte is sufficient to provide a diagnosis.

12. The method of claim 11 further comprising the step of treating the cell suspension to minimize cell clumping and lysis prior to conducting step (i).

13. The method of claim 11 further comprising the step of repeating at least step (iv) to form the cell array.

14. The method of claim 11 further comprising the step of substantially covering the cell array with a cover fluid prior to performing step (b), wherein the cover fluid is selected from the group consisting of inert liquids, immiscible liquids, and mineral oil.

15. The method of claim 11, wherein the diagnostic analysis is an immunohistochemistry assay and the test reagent is an antibody probe.

16. The method of claim 11, wherein the diagnostic analysis is fluorescent in situ hybridization and the test reagent is a nucleic acid probe.

17. The method of claim 11, wherein the diagnostic analysis is cytogenetic analysis and the test reagent is a chromosome stain.

18. The method of claim 17, wherein step (c) further comprises heating at least one discrete cell sample arranged on the substrate.

* * * * *